United States Patent [19]

Gelling et al.

[11] Patent Number: 6,153,800
[45] Date of Patent: Nov. 28, 2000

[54] PROCESS FOR THE PREPARATION OF AN ALDEHYDE

[75] Inventors: Onko J. Gelling, Stein; Peter C. Borman, Geleen; Petrus W. N. M. Van Leeuwen, Kockengen, all of Netherlands

[73] Assignees: DSM N.V., Heerlen, Netherlands; E.I. du Pont de Nemours and Company, Wilmington, Del.

[21] Appl. No.: 09/303,680

[22] Filed: May 3, 1999

Related U.S. Application Data

[63] Continuation of application No. PCT/NL97/00595, Oct. 30, 1997
[60] Provisional application No. 60/032,672, Dec. 9, 1996.

[30] Foreign Application Priority Data

Apr. 11, 1996 [NL] Netherlands ........................ 96203070

[51] Int. Cl.$^7$ .................................................. C07C 45/50
[52] U.S. Cl. .......................................... 568/454; 568/451
[58] Field of Search ..................................... 568/451, 454

[56] References Cited

U.S. PATENT DOCUMENTS

| | | | |
|---|---|---|---|
| 4,169,861 | 10/1979 | Hughes | 260/604 |
| 4,260,828 | 4/1981 | Morell et al. | 568/454 |
| 5,234,113 | 8/1993 | Ramey | 211/59.4 |
| 5,391,801 | 2/1995 | Sato et al. | 558/156 |
| 5,663,369 | 9/1997 | Kreutzer et al. | 549/212 |
| 5,874,641 | 2/1999 | Burke et al. | 568/454 |

FOREIGN PATENT DOCUMENTS

| | | |
|---|---|---|
| 0518241 A2 | 12/1992 | European Pat. Off. . |
| WO 96/11182 | 4/1996 | WIPO . |

*Primary Examiner*—Sreeni Padmanabhan
*Attorney, Agent, or Firm*—Pillsbury Madison & Sutro Intellectual Property Group

[57] ABSTRACT

Process for the preparation of an aldehyde through hydroformylation of an unsaturated organic compound in the presence of a catalyst system comprising rhodium of iridium and a multidentate organic phosphite ligand, wherein a monodentate phosphine is present.

The process according to the invention can advantageously be carried out for the preparation of methyl-5-formylvalerate, which is an intermediate product in the preparation of a caprolactam or adipic acid, which are in turn raw materials for the preparation of nylon-6 and nylon-6,6, respectively.

18 Claims, 1 Drawing Sheet

PROCESS FOR THE PREPARATION OF AN ALDEHYDE

CROSS REFERENCE TO RELATED APPLICATIONS

This application is a continuation of international application PCT/NL97/00595 which designated the United States of America and was filed on Oct. 30, 1997. This application also claims the benefit of U.S. provisional application 60/032,672, filed Dec. 9, 1996.

FIELD OF THE INVENTION

The invention relates to a process for the preparation of an aldehyde through hydroformylation of an unsaturated organic compound in the presence of a catalyst system comprising rhodium or iridium and a multidentate organic phosphite ligand.

BACKGROUND OF THE INVENTION

Hydroformylation is the reaction of an unsaturated compound with hydrogen and carbon monoxide to give an aldehyde compound in the presence of a catalyst system.

Such a process is described in WO-A-9518089. WO-A-9518089 describes the preparation of methyl-5-formylvalerate through hydroformylation of methyl-3-pentenoate in the presence of a catalyst system containing rhodium and a multidentate organic phosohite ligand.

A drawback of this process is that the multidentate phosphite ligand proves to be sensitive to degradation in the presence of traces of oxygen or other oxidising compounds, for example hydroperoxide compounds, which may be present during the reaction. Oxygen may for example leak into a continuously operating process. Degradation of the ligand is a disadvantage because fresh ligand has to be added to the system to ensure that the activity and selectivity to aldehyde compounds of the reaction remain at the required level for a longer period. Adding such large amounts of fresh ligand per kg of aldehyde product is not attractive from an economic viewpoint, in view of the relatively high cost price of this type of phosphite ligand and hence of the aldehyde product.

The object of this invention is a process in which, in the presence of traces of oxygen, less phosphite ligand is consumed per kg of aldehyde product than in the process according to the state of the art.

This object is achieved in that a monodentate phosphine is present.

SUMMARY OF THE INVENTION

It has been found that with the process according to the invention less multidentate phosphite ligand is consumed per kg of aldehyde product while the selectivity of the reaction remain at virtually the same level. This was unexpected, because monodentate phosphines are well known ligands and it was expected that by adding these extra ligands the selectivity to (linear) aldehyde compounds would be adversely effected.

An additional advantage of the process according to the invention is that the relatively expensive multidentate phosphite ligand is protected, as it were, by the addition of a monodentate phosphine. Although the phosphine is selectively oxidised in the process according to the invention, this is not disadvantageous because the phosphine is much cheaper than the phosphite. The aforementioned advantages are further enhanced if the process for the preparation of an aldehyde through hydroformylation of an unsaturated organic compound is carried out as a continuous process. Being able to reuse the catalyst system several times, without the selectivity being adversely affected, is an extremely important factor in a continuous process.

DETAILED DESCRIPTION OF THE INVENTION

Figure 1:
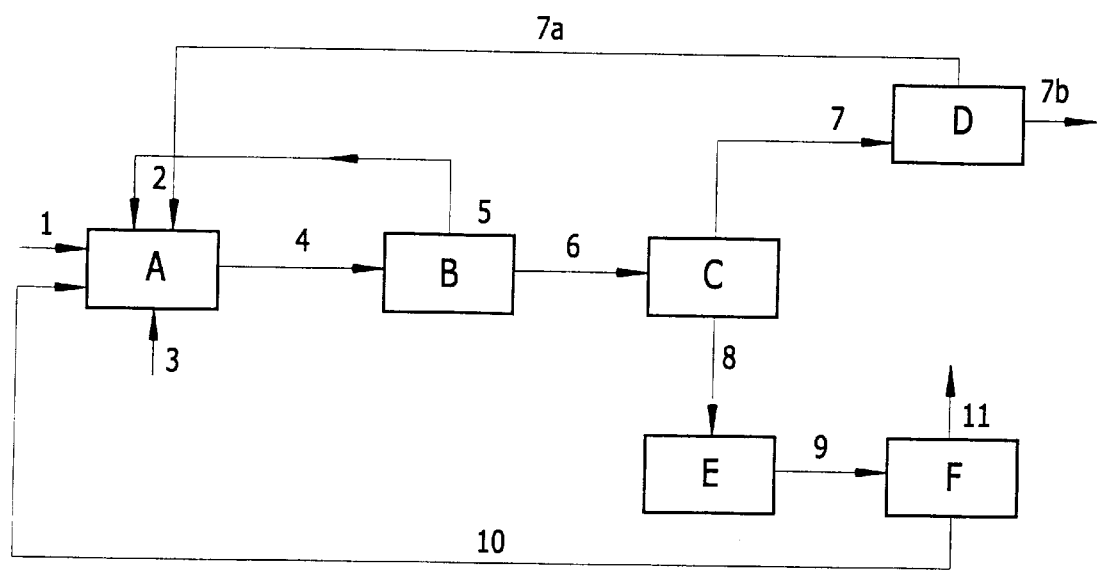
FIG. 1 is a schematic representation of a process according to the invention.

U.S. Pat. No. 4,169,861 describes the preparation of an alkanal through hydroformylation of an alpha-olefin in the presence of a catalyst system containing rhodium, a bidentate phosphine ligand and a monodentate phosphine ligand, the monodentate ligand being a phosphine with a steric parameter θ of between 135° and 150°. It does not mention a multidentate phosphite ligand as part of the catalyst system.

Without wishing to restrict itself to the following theory, the applicant expects that the decomposition of the multidentate phosphite ligand is attributable to the presence of oxygen in the hydroformylation reaction and/or in the further processing of the resulting reaction mixture. The starting materials and/or solvents may for example contain traces of oxygen. Oxygen may for example also be present in the process equipment of a commercial hydroformylation process due to leakage into the equipment.

The ligand's sensitivity to oxygen was found to be particularly high when a $C_1$–$C_6$-alkyl ester of 3-pentenoic acid (alkyl pentenoate) is used as a starting material, as described in EP-A-662468. Hydroperoxide compounds may be formed as a result of the reaction of the oxygen with the alkyl pentenoates.

The monodentate phosphine according to the invention can be represented by the general formula P(R')$_3$, where the R' groups are organic groups. Preferably the organic group R' is an aliphatic, alicyclic or aromatic group with 1–20 carbon atoms, preferably 5–12 carbon atoms, and the three R' groups may be the same or different. The R' group may contain one or more hetero atoms, for example oxygen, nitrogen or a halogen.

Examples of monodentate phosphines according to the invention are trimethylphosphine, triethylphosphine, tributylphosphine, tripropylphosphine, tri(propylnitrile) phosphine, diethylphenylphosphine, diphenylmethylphosphine, diphenylethylphosphine, tri(trifluoromethyl)phosphine, tri(isobutyl)phosphine, triphenylphosphine, tri(p-tolyl)phosphine, tri(m-fluorophenyl)phosphine, isopropyldiphenylphosphine, tri(isopropylphosphine), tri(sec-butyl)phosphine, tribenzylphosphine, tricyclohexylphosphine, dicyclohexylphenylphosphine, di(t-butyl)phenylphosphine, trineopentylphosphine, tri(r-butyl)phosphine, tri(o-methoxyphenyl)phosphine, tri(pentafluorophenyl) phosphine, tri(o-tolyl)phosphine and trimesitylphosphine. A mixture of two or more of these compounds is also suitable for use as the monodentate phosphine.

It has been found that in the process according to the invention the organic groups R' of the PR'$_3$ phosphine are preferably chosen so that the steric parameter θ of the phosphine is between 160° and 220°, preferably between 170° and 210°. It has been found that the activity of the reaction is not adversely effected when using these phosphine compounds.

The steric parameter θ is the top angle of a cylindrical cone, centred at 2.28 Å ($10^{-10}$ m) from the centre of the phosphorus atom, which just touches the Van der Waals radii of the outer atoms of the R' substituents of a symmetrical P(R')$_3$-phosphine (see also "Chemical Reviews, 1977, Volume 77, pp. 313–348" by C. A. Tolman and U.S. Pat. No. 4169861).

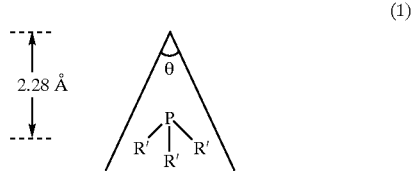

(1)

The steric parameter θ of an asymmetrical PR'$_3$-phosphine in which at least one of the three R' groups differs from the other R' groups, for example PR'R''R''', can be calculated with the aid of the top angles of the corresponding symmetrical phosphines PR'$_3$, PR''$_3$ and PR'''$_3$ using the following formula:

$$\theta(P(R')(R'')(R''')) = 2/3 \frac{\theta(P(R')_3)}{2} + \frac{\theta(P(R'')_3)}{2} + \frac{\theta(P(R''')_3)}{2} \qquad (2)$$

Examples of such monodentate phosphines having a steric parameter θ of between 160° and 220° have been mentioned above. Preferably, the monodentate phosphine having a steric parameter θ of between 160° and 220° is trineopentylphosphine, tri(t-butyl)phosphine or tri(o-tolyl)phosphine.

Most preferably, tri(o-tolyl)phosphine is used as the monodentate phosphine in the process according to the invention. Tri(o-tolyl)phosphine is cheap, readily obtainable and shows a high effectiveness in small amounts.

The monodentate phosphine can be added to the hydroformylation mixture or it may already be present in a reaction mixture which also contains the unsaturated organic compound, rhodium or iridium and a multidentate phosphite ligand.

The concentration of monodentate phosphine in the hydroformylation mixture according to the invention is preferably an effective amount sufficient to preclude substantial degradation of the multidentate phosphite ligand. In particular, the amount is between 1 and 40 mol per mol of the multidentate phosphite ligand, preferably between 2 and 10 mol per mol of the multidentate phosphite ligand.

The multidentate phosphite ligand preferably has the following general structure:

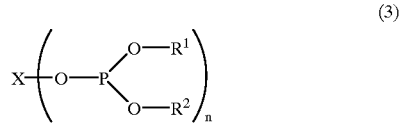

(3)

where n is 2–6, X is an n-valent organic bridging group and $R^1$ and $R^2$ are independently two organic monovalent aryl groups and/or one divalent diaryl group.

$R^1$ and $R^2$ are preferably monovalent organic groups with 1 to 20 carbon atoms or $R^1$ and $R^2$ form together one divalent organic group having 6 to 30 carbon atoms. Most preferably, $R^1$ and $R^2$ are monovalent aryl groups having 6 to 14 carbon atoms. The different $R^1$ and R2 groups in the ligand may be different. For example in the same ligand some groups $R^1$ and $R^2$ may be divalent groups while other groups $R^1$ and $R^2$ are monovalent groups.

X is preferably an organic group having between 1 and 40 carbon atoms, and more preferably between 6 and 30 carbon atoms. An example of a ligand having a tetravalent organic group is a ligand having a bridging group corresponding to pentaerythritol. Bidentate ligands, having a bivalent bridging group, are most frequently mentioned in the patent literature. Examples of such phosphite ligands are described in U.S. Pat. No. 4,748,261, EP-A-556681 and EP-A-518241.

When internally ethylenically unsaturated organic compounds, for example 2-butene or 3-pentenoate, are used as a starting material to prepare terminal aldehydes, use is preferably made of a multidentate phosphite ligand that can form a chelate-type complex with the metal employed (rhodium or iridium) in the reaction zone. A chelate-type complex is understood to mean that (substantially) at least two phosphorus P atoms of a ligand molecule form a coordinated bond with one rhodium or iridium atom/ion. A non-chelate-type complex is understood to mean that only one phosphorus 2 atom of a ligand molecule forms a coordinated bond with one rhodium or iridium atom/ion. The choice of bridging group X of the ligand will determine whether a chelate-type complex can be formed in the reaction zone. Examples of bridging groups that result in a ligand that can form a chelate-type bridging group are for example described in WO-A-9518089.

A preferred ligand for use in the process according to the invention has a 2,2'-dihydroxy-1,1'-binaphthalene bridging group, which bridging group is preferably substituted at the 3 and 3' positions. This ligand can be represented by the following general formula:

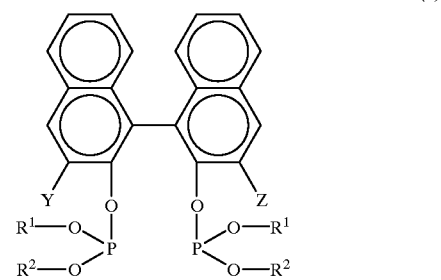

(4)

where Y and Z are substituents other than hydrogen and $R^1$ and $R^2$ are the same or different substituted monovalent aryl groups and/or any one of $OR^1$ and $OR^2$ connected to one phosphorus atom forms an —O—$R^3$—O-group, where $R^3$ is a divalent organic group containing one or two aryl groups.

The substituents Y and Z are preferably organic groups containing at least one carbon atom, more preferably containing 1–20 carbon atoms.

Preferably, Y and Z are individually selected from the group comprising alkyl, aryl, triarylsilyl, trialkylsilyl, carboalkoxy, carboaryloxy, aryloxy, alkoxy, alkylcarbonyl, arylcarbonyl, oxazole, amide, amine or a nitrile.

For Y and Z, the alkyl group is preferably a $C_1$–$C_{10}$ alkyl group, for example methyl, ethyl, propyl, isopropyl, butyl, tert-butyl, isobutyl, pentyl or hexyl. An example of a suitable triarylsilyl group is triphenylsilyl and examples of a suitable trialkylsilyl group are trimethylsilyl and triethylsilyl. Preferred aryl groups have 6 to 20 carbon atoms, for example phenyl, benzyl, tolyl, naphthyl, anthranyl or phenanthryl. Preferred aryloxy groups have 6 to 12 carbon atoms, for example phenoxy. Preferred alkoxy groups have 1 to 20 carbon atoms, for example methoxy, ethoxy, tert-butoxy or isopropoxy. Preferred alkylcarbonyl groups have 2 to 12 carbon atoms, for example methylcarbonyl, tert-butylcarbonyl. Preferred arylcarbonyl groups have 7 to 13 carbon atoms, for example phenylcarbonyl. Preferred amide groups contain a $C_1$–$C4$ alkyl group and preferred amine groups contain two $C_1$–$C_5$ alkyl groups.

Most preferably, Y and Z are individually a carboalkoxyl or a carboaryloxy group, —$CO_2R$, in which R is a $C_1$–$C_{20}$ alkyl group or a $C_6$–$C_{12}$ aryl group and preferably a $C_1$–$C_8$ alkyl group. Examples of suitable R groups are methyl, ethyl, propyl, isopropyl, n-butyl, tert-butyl, isobutyl, phenyl and tolyl. Even more preferably, Y and Z are both the same carboaryloxy and more preferably the same carboalkoxyl group because the resulting ligands are more easily obtainable.

The 2,2'-dihydroxy-1,1'-binaphtalene bridging group can optionally be further substituted with other groups, for example halogen, for example Cl or F or one of the substituents R which may be present on the bridging group as described above.

$R^1$ and $R^2$ are preferably the same or different monovalent aryl groups, and more preferably aryl groups with 6 to 20 carbon atoms. It is to be understood that all four $R^1$ and $R^2$ groups can be different. Preferably all four groups are the same because the resulting ligands are more readily available. Alternatively, $OR_1$ and $OR^2$ (connected to the same P atom) can form an —O—$R^3$—O-group, where $R^3$ is a divalent group of 6 to 40 carbon atoms containing one or two aryl groups. Preferably, $R^1$ and $R^2$ are monovalent aryl groups, for example phenyl, containing at least one group, $R^4$, other than hydrogen in an ortho position relative to the oxygen atom, where $R^4$ is a $C_1$ to $C_{20}$ alkyl or $C_6$–$C_{20}$ aryl group and preferably a $C_1$–$C_6$ alkyl group. Other preferred monovalent aryl groups for $R^1$ and $R^2$ are monovalent fused aromatic ring systems with 2 or more rings having 10–20 carbon atoms. $R_1$ and $R^2$ can optionally be further substituted with for example $C_1$–$C_{10}$ alkyl, $C_6$–$C_{20}$ aryl, $C_1$–$C10$ akoxy or $C_6$–$C_{20}$ aryloxy groups or halogen groups, for example F, Cl or Br or amine groups.

When the aryl groups $R^1$ and $R^2$ are substituted with at least one $R^4$ group at the ortho position relative to the phenolic oxygen atom, a higher linear selectivity is observed when these ligands are used in a hydroformylation process. Examples of these $R^4$ groups are methyl, ethyl, propyl, isopropyl, isobutyl, tert-butyl or n-butyl. For $R^4$ preferably only one bulky group, having a steric hinderance of isopropyl or greater, is ortho-substituted on the aryl group. When less bulky substituents are used, both ortho positions are preferably substituted with these groups. The preferred $R^4$-substituted aryl group for $R^1$ and $R^2$ is 2-isopropylphenyl or 2-tert-butylphenyl group.

Another preferred class of aryl groups for $R^1$ and $R^2$ comprises fused aromatic ring systems with 2 or more rings having 10 to 20 carbon atoms which do not necessarily have to be substituted at the ortho position (on the carbon atom adjacent to the carbon atom which is bonded to the oxygen atom in formula (4) with groups other than hydrogen. It has been found that when $R^1$ and/or $R^2$ is such an unsubstituted aromatic ring system, a high catalyst activity, a high selectivity to terminal aldehyde and a high linearity can be achieved. Examples of such fused aromatic ring systems are phenanthryl, anthryl and naphthyl groups. Preferably 9-phenanthryl or 1-naphthyl groups are used. The aromatic ring systems can optionally be substituted with for example the aforementioned substituents, for example at the positions of the ring systems other than the ortho position described above.

Examples where $R^1$ and $R^2$ are linked to form divalent groups $R^3$ are $C_6$–$C_{25}$ diaryl groups, for example a 2,2'-diphenyldiyl or 2,2'-dinaphtyldiyl group.

These ligands may be prepared using a variety of methods known in the art; see for example descriptions in U.S. Pat. No. 4,769,498; U.S. Pat. No. 4,688,651 and J. Amer. Chem. Soc., 1993, 115, 2066. The organic bidentate phosphite compounds according to the invention can be prepared with the 3- or 3,3'-substituted 2,2'-dihydroxy-1,1'-binaphthalene bridging compounds. The binaphthol bridging compounds can be prepared by means of procedures as described in Tetrahedron Lett. 1990, 31(3), 413–416 or in J. Am. Chem. Soc. 1954, 76, 296 and Org. Proc. Prep. International, 1991, 23, 200. The phosphite compounds can be prepared by using the process described in the aforementioned U.S. Pat. No. 5,235,113 to couple these binaphthol bridging compounds with phosphoro-chloridites, $(R^1O)(R^2O)PCl$, prepared by treating $R^1OH$ and/or $R^2OH$ with $PCl_3$.

The catalyst system used in the process according to this invention can be prepared by mixing a suitable rhodium or iridium compound with the phosphite ligand, optionally in a suitable solvent, in accordance with well-known complex-forming methods. The solvent will generally be the solvent used in the hydroformylation. Suitable rhodium and iridium compounds are for example hydrides, halides, organic acid salts, acetylacetonates, inorganic acid salts, oxides, carbonyl compounds and amine compounds of these metals. Examples of suitable catalyst precursors are $Ir(CO)_2(acac)$, $Ir_4(CO)_{12}$, $Rh(OAc)_3$, $Rh_2O_3$, $Rh(acac)(CO)_2$, $Rh(CO)_2$ (DPM), $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$, (where "acac" is an acetylacetonate group; "Ac" is an acetyl group; "COD" is 1,5-cyclooctadiene; and "Ph" is a phenyl group, DPM is a 2,2,6,6-tetramethyl-3,5-heptanedionate group). However, it should be noted that the rhodium and iridium compounds are not necessarily limited to the compounds listed above.

The metal is preferably rhodium.

The process according to the invention is especially advantageous when preparing terminal (or linear) aldehyde compounds.

The unsaturated organic compound that is hydroformylated to form an aldehyde according to the process according to the invention has at least one ethylenically unsaturated ("C=C") bond in the molecule and usually between 2 and 20 carbon atoms. Examples of suitable unsaturated organic compounds are linear, terminally unsaturated olefins, for example ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; branched, terminally unsaturated olefines, for example isobutene and 2-methyl-1-butene; linear, internally unsaturated olefins, for example cis- and trans-2-butene, cis- and trans-2-hexene, cis- and trans-3-hexene, cis- and trans-2-octene and cis- and trans-3-octene; branched, internally unsaturated olefins, for example 2,3-dimethyl-2-butene, 2-methyl-2-butene and 2-methyl-2-pentene; mixtures of terminally unsaturated olefins and internally unsaturated olefins, for example octenes prepared through dimerisation of butenes, olefine-oligomer-isomer mixture of dimer to tetramer of lower olefins including propylene, n-butene, isobutene; and cycloaliphatic unsaturated olefins, for example cyclopentene, cyclohexene, 1-methylcyclohexene, cyclooctene and limonene.

Suitable unsaturated organic compounds are also olefins with an aromatic substituent, for example styrene, alpha-methylstyrene and allylbenzene; diene compounds, for example 1,5-hexadiene, 1,7-octadiene and norbornadiene, are also suitable unsaturated olefins.

The unsaturated organic compound may be substituted with one or more functional groups. The functional groups contain one or more hetero atoms, which may be the same or differ from one another, for example oxygen, sulphur, nitrogen or phosphorus. Examples of these unsaturated organic compounds are vinyl methyl ether, methyloleate, oleyl alcohol, methyl-2-pentenoate, methyl-3-pentenoate, methyl-4-pentenoate, 3-pentenoic acid, 4-pentenoic acid, 2-pentene nitrile, 3-pentene nitrile, 4-pentene nitrile, 2-pentenal, 3-pentenal, 4-pentenal, 4-hydroxy-1,7-octadiene, 1-hydroxy-3,7-octadiene, 1-methoxy-3,7-octadiene, 7-octen-1-al, acrylonitrile, esters of acrylic acid, methacrylate, ester of methacrylic acid, methylmethacrylate, vinyl acetate and 1-acetoxy-3,7-octadiene.

The process according to the invention can be carried out in a particularly advantageous manner by using as a starting material internally unsaturated olefins with between 4 and 20 carbon atoms in a process to prepare terminal (linear) aldehyde compounds. Examples of such internally unsaturated olefins have been mentioned above. Preferably, use is made of internally unsaturated olefins substituted with one or more functional groups according to formula (5):

$$CH_3-CR^5=CR^6-R^7 \qquad (5)$$

where $R^5$ and $R^6$ are a hydrocarbon group or preferably hydrogen and $R^7$ is a cyanide group or a hydrocarbon group, whether or not substituted with one or more functional groups which contain a hetero atom, for example oxygen, sulphur, nitrogen or phosphorus. Preferably, use is made of internally unsaturated olefins having between 4 and 20 carbon atoms according to formula (5), where $R^5$ and $R^6$ are hydrogen.

Examples of internally unsaturated olefins having between 4 and 20 carbon atoms according to formula (5), where $R^5$ and $R^6$ are hydrogen, are 2-pentene nitrile, 3-pentene nitrile, 3-perntenoic acid and $C_1-C_6$-alkyl ester of 3-pentenoic acid. It has been found that these compounds can be well converted into the corresponding linear aldehyde compounds using the process according to the invention. These aldehyde compounds, in particular methyl-5-formylvalerate, are intermediate products in the preparation of ε-caprolactam or adipic acid, which are in turn raw materials or the crecaration of nylon-6 and nylon-6,6, respectively. Examples of $C_1-C_6$-alkyl-3-pentenoate esters are methyl-, ethyl- propyl-, isopropyl-, tert-butyl-, pentyl- and cyclohexyl-3-pentenoate. Preferably, use is made of methyl- and ethyl-3-pentencate, because these compounds a readily obtainable. 3-penrene nitrile, 3-pentenoic acid and $C_1-C_6$ -alkylesters of pentenoic acid may be present in the reaction mixture as a mixture which also comprises 2- and 4-pentene nitrile, 2- and 4-pentenoic acid and $C_1-C_6$-alkylesters of 2- and 4-pentenoic acid, respectively.

The concentration of rhodium or iridium (compound) in the reaction mixture may, vary, from 1 to 5000 ppm medium or iridium. Preferably, the concentration is between 50 and 1000 ppm.

The molar ratio of the multidentate phosphite ligand to rhodium or iridium is generally from 0.5 to 100 and preferable from 1 to 10 most preferably less than 1.2 (mol ligand /mol metal). Preferably the ratio is higher than 1.05. Small deviations in ligand of rhodium concentration will then not automatically result in a lower yield to the aldehyde compound. It has been found that by performing the process according to the invention with such a slight molar excess of ligand to rhodium the ligand degradation rate is further decreased. When performing the process with a slight excess of ligand to rhodium (or iridium) it will be preferred to monitor the concentration and degradation, due to other causes than oxidation, of the ligand during the course of the continuous process and add fresh ligand in order to remain in the preferred ranges of operation.

The reaction mixture may serve as a solvent in the process according to the invention, so that as a rule the addition of an additional solvent is not necessary. The reaction mixture is a mixture of the reactants of the hydroformylation, for example the unsaturated organic compound, the aldehyde and/or by-products formed, in particular the by-products with high boiling temperatures. If an additional solvent is added, a saturated hydrocarbon, for example naphtha, kerosine, mineral oil or cyclohexane, or an aromatic compound, for example toluene, benzene, xylene, or an ether, for example diphenylether, tetrahydrofuran, or a ketone, for example cyclohexanone, or a nitrile, for example benzonitrile, texanol® or tetraglyme® (Union Carbide), is suitable for use as additional solvent. A mixture of two or more of these compounds is also suitable for use as additional solvent.

The reaction conditions of the hydroformylation reaction in the process according to the invention will be dependent of the particular starting unsaturated organic compound.

The temperature is generally between room temperature and 200° C., preferably between 50° C. and 150° C.

The pressure is generally between 0.1 MPa and 20 MPa, preferably between 0.15 MPa and 10 MPa and most preferably between 0.2 MPa and 1 MPa.

The molar ratio of hydrogen and carbon monoxide is generally between 10:1 and 1:10, preferably between 6:1 and 1:2.

The reaction according to the invention can be carried out in a gas/liquid contactor known to a person skilled in the art. Examples of suitable reactors are bubble column, screen-plate column, gas-liquid agitated reactor.

The process according to the invention can be carried out batchwise or, preferably, in a continuous process. In a commercial process the reaction is preferably carried out in a continuous mode. The continuous process can be started by for example dosing the rhodium or iridium compound, the multidentate phosphite ligand and the monodentate phosphine to a reactor in one operation and, after the temperature has risen, adding the unsaturated organic compound, carbon monoxide and hydrogen to the reaction mixture in continuous mode or with interruptions. The reactor effluent contains the aldehyde product, the rhodium or iridium compound, the multidentate phosphite ligand, the monodentate phosphine, phosphine-oxide, carbon monoxide, hydrogen and the solvent optionally used. Carbon monoxide and hydrogen can be separated from the reaction mixture, by reducing in the pressure to for example 0.1 MPa. The aldehyde can be removed from the resulting mixture in one or more separation steps. The rhodium or iridium compound, the multidentate phosphite, monodentate phosphine and phosphine-oxide are preferably recycled to the reactor and reused in the process according to the invention. The separation steps are preferably carried out through distillation at a pressure of 0.001–1 MPa, most preferably through vacuum distillation at a pressure of 0.01–0.1 MPa, for example in a rolled film evaporator. Another suitable separation method is membrane separation as for example described in WO-A-9634687.

The aldehyde product can be separated from this reaction mixture using any separation technique known to a person skilled in the art. Examples of suitable separation techniques are (vacuum) distillation, crystallisation and extraction using a suitable extraction agent.

The concentrations of the phosphine and of the phosphite are preferably measured continuously or regularly. If the concentration drop below the desired value, as a result of for example degradation of these compounds, fresh compound is added to the recirculating reaction mixture. It has been found that the degradation products of the phosphine do not adversely affect the activity and the selectivity of the hydroformylation reaction.

Preferably, the recirculating catalyst system is contacted with a Lewis base as described in EP-A-285136. Most preferably the Lewis base is an ion exchanger with basic groups, for example a packed bed of a polystyrene matrix containing basic groups (for example Amberlist A21®).

A possible process according to the invention, as used in the examples, is schematically represented in FIG. 1. FIG. 1 will be elucidated in a non-limitative manner below to illustrate the preparation of methyl-5-formylvalerate using a rhodium/phosphite catalyst system.

In FIG. 1, methyl-3-pentencate is fed to reactor (A) via stream (1). In Reactor A the catalyst system is present. A mixture of CO and $H_2$ is fed to the reactor (A) via stream (2) and fresh monodentate phosphine is continuously or batchwise fed to reactor (A) via stream (3). The effluent of reactor (A) comprising methyl-5-formylvalerate, by-products, any unconverted methyl-3-pentenoate, the catalyst system, phosphine, carbon monoxide and hydrogen is fed to flasher (B) via stream (4). In the flasher (B) the pressure is reduced to for example atmospheric pressure. Carbon monoxide and hydrogen are separated from the reaction mixture via stream (5) and recycled to the reactor (A). The resulting liquid mixture is fed to separation step (C) via resulting liquid stream (6). In separation step (C) the mixture is subjected to a vacuum distillation. Most of the volatile components, for example methyl-2-pentenoate, methyl-4-pentenoate, methylacrylate, most of the unconverted methyl-3-pentenoate and a small part of the aldehyde products are discharged via stream (7). Stream (7) is fed to separation step D. In separation step D methylacrylate, methyl-4-pentenoate and cis-methyl-2-pentenoate are discharged via stream (7b). Trans-methyl-2-pentenoate and methyl-3-pentenoate are recirculated to reactor (A) via stream (7a). The residual mixture of separation step (C) is fed to ion exchanger (E), a packed bed of a polystyrene matrix containing basic amine groups, via stream (8). The effluent (9) is fed to separation step (F). In separation step (F) the remainder of the unreacted methyl-3-pentenoate, the methyl-5-formylvalerate and branched isomers are separated from the catalyst system, the monodentate phosphine and by-products by means of vacuum distillation. The residue is recycled to reactor (A) via stream (10).

Preferably, purge flows are present in the process to prevent an accumulation of by-products and the degradation products of the phosphine and the phosphite compounds. These purge flows mostly comprise an amount of the rhodium/phosphite catalyst system. The concentration of rhodium in such a purge flow will generally be higher than 100 ppm rhodium and lower than 2000 ppm rhodium. For a commercially interesting process it is necessary to recover the catalyst system comprising the rhodium/phosphite ligand complex from such a purge flow. The rhodium/phosphite ligand complex can advantageously be recovered from such purge flows using a membrane separation process as described in WO-A-9634687. To prevent confusion, these purge flows are not shown in the figure.

Methyl-5-formylvalerate and branched isomers are discharged via stream (11). Methyl-5-formylvalerate, may be further purified by e.g. distillation. The ion exchanger E may also be positioned elsewhere in the process other than between separation steps (C) and (F), for example between reactor (A) and flasher (B) or between flasher (B) and separation step (C) or between (F) and (A). Because the degradation and or loss via purges of the phosphite ligand cannot be avoided fresh catalyst system will have to be supplied to the recirculating catalyst system.

The invention also relates to a catalyst system comprising a group 8–10 metal, a multidentate organic phosphite ligand as described above and a monodentate phosphine, which monodentate phosphine can be represented by the general formula $FR'_3$. The organic (R') groups are preferably as described above. The organic groups R' of the $PR'_3$ phosphine are preferably chosen so that the steric parameter θ of the phosphine is between 160° and 220°, preferably between 170° and 210°.

The metal present in the catalyst system according to the invention is preferably rhodium. This catalyst system is particularly advantageous if it is used in the hydroformylation of internally unsaturated olefins as described above.

The catalyst system according to the invention can for example also be used as a hydrocyanation, hydrogenation, polymerisation, isomerisation and carbonylation catalyst.

The invention will be further elucidated by means of the following, non-limiting examples. The conversion of methyl-3-pentenoate (M3P) is the percentage of M3P reacted. The selectivity to methyl-5-formylvalerate (M5FV) can be as follows calculated: the amount (in mol/h) of M3P which has been converted to M5FV is divided by the amount (in mol/h) of M3 which has been reacted.

EXAMPLE I

A Hastalloy B autoclave ((A) in FIG. 1) with a volume of 1 l was loaded with a 200 g catalyst solution. The catalyst solution consisted of : 568 g m-xylene, 1.105 g (4.3 mmol) rhodium dicarbonyl acetylacetonate ($Rh(acac)(CO)_2$), 20.0 g (65.8 mmol) tri-(ortho-tolyl)phosphine and 14.0 g (12.8 mmol) of a bidentate phosphite ligand ($M_w$=1090) with formula (5)

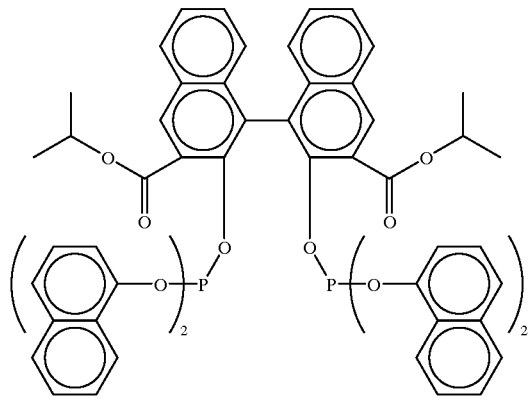

To the autoclave (the reactor) was also added 300 g of methyl-3-pentenoate (M3P) (stream (1) in FIG. 1). The reactor was heated under 1 MPa $CO/H_2$ pressure (1:1 mol/mol $CO/H_2$) to 95° C. The $CO/H_2$ was constantly fed to the reactor (stream (2) in FIG. 1) in such a way that there was always an off-gas stream from the reactor. The reactor could contain approximately 500 ml liquid. As soon as the reactor contained more than approximately 500 ml, it overflowed via a dip tube and the excess of reaction mixture was removed (stream (4) in FIG. 1). The reactor effluent stream existing of liquid in excess of 500 ml and unreacted gasses was let down to atmospheric pressure via a back pressure regulator and fed into a gas liquid separator ((B) in FIG. 1). The gas was—after passing through a condenser to 1 bar to remove condensables—vented (stream (5) in FIG. 1). The liquid was collected in the bottom of the gas liquid separator from where it is fed (stream (6) in FIG. 1) through a control valve to the first short path rolled film evaporator ((C) in FIG. 1). In this evaporator most of the unreacted M3P, light by-products and a small part of the aldehyde products are under vacuum (78947 Pa at 90° C. wall temperature). The liquid residue (stream (8) in FIG. 1) passes through a column filled with filled with an amount of 7 g of a weakly basic Amberlist A21 resin (9) in FIG. 1). From there it is pumped (stream (9) in FIG. 1) to a second short path rolled film evaporator ((F) in FIG. 1). In this evaporator the remainder of the unreacted M3P and a part of the MFV products are evaporated under a higher vacuum (13158 Pa at 90° C. heating temperature). The residue of the second evaporator was pumped back (stream (10) in FIG. 1) into the reactor thereby closing the loop. The temperature and pressure of both evaporators are adjusted such that at a stable running situation: a constant total liquid inventory on the set up, is maintained. (Approx. 1200 ml if calculated back to reactor liquid prior to distillation.) After 2 hours of reaction at 95° C. fresh M3P (stream (1) in figure) was pumped into the reactor at a rate of 90 g/h and also more catalyst solution as pumped in at a rate of 80 g/h. CO and $H_2$ are fed at a flow-rate of 30 Nl/h (stream (2) in figure). The pressure is set at 0,5 MPa. In approx. 4 hours all the distillations and pumps are operating and the catalyst feed is stopped. After another 16 hours the set-up reaches a steady state. At the stable point the Rh concentration in the reactor is approximately 300 ppm. The Rh/phosphite molar ratio is 1/3 and the phosphine/phosphite molar ratio is 5/1. Once every 24 h a liquid sample is taken from the gas-liquid separator. This was done very carefully excluding contact with oxygen and moisture using a sample taker which as carefully opened in a dry-box making up the the samples for all kinds of analysis. The samples were analysed for organic and inorganic components using gaschromatography GC, high pressure liquid chromatography (HPLC), nuclear magnetic resonance (NMR) and Elemental analysis. 210 hours into the experiment the composition of the liquid in the reactor was determined as: 0.39 wt. % methyl-4-pentenoate, 0.06 wt. % methyl-cis-2-pentenoate, 1.82 wt. % methyl valerate, 9.17 wt. % methyl-trans-3-pentenoate, 2.61 wt. % methyl-cis-3-pentenoate, 4.48 wt. % methyl-trans-2-pentenoate, 0.04 wt. % xylene, 0.48 wt. % methyl-2-formylvalerate, 1.06 wt. % methyl-3-formylvalerate, 1.61 wt. % methyl-4-formylvalerate, 71.89 wt. % methyl-5-formylvalerate (M5FV), 0.23 wt. % monomethyladipate, 0.48 wt. % aldol condensation products, 0.64 wt. % tri(ortho-tolyl)phosphine, 0.44 wt. % tri(ortho-tolyl)phosphine-oxide and 4.6 wt. % of heavies and catalyst components.

To ensure that the substrate is free of hydroperoxides the M3P is batch distilled at atmospheric pressure over triphenylphosphine and fed over a column filled with alumina-oxide prior to feeding it to the reactor. The distillates were continuously collected and analysed for product composition.

The reaction could be run for 250 h without significant phosphite degradation by oxidation. But the tri(ortho-tolyl) phosphine was oxidised for 68% at the end of the run. Selectivity during the run changed from 84 to 82%. The conversion changed a little because of sampling from the set-up going from 79 to 77%.

Comparative Experiment A

Example I was repeated, except that no tri(ortho-tolyl) phosphine was added to the catalyst solution. In this run the reaction could be run for 110 h at a degree of conversion of 80%, with a selectivity of 82% to M5FV, relative to M3P. After 110 hours of operation,the concentration of the phosphite ligand starting material dropped to below stoichiometric in reference to rhodium. The reaction rate increased significantly (the conversion increased to 90%) and the selectivity (to iM5FV) dropped dramatically (to 40%). It was found that all the excess ligand had been degraded, largely as a result of oxidation reactions, as indicated by $^{13}P$ NMR.

EXAMPLE II

Example I was repeated, except that triphenylphosphine was added to the catalyst solution instead of tri(ortho-tolyl) phosphine. The Rh/triphenylphosphine ratio was 1/10 on a molar basis. The reaction had the following characteristics: the reaction could be run for the whole run of 250 h without significant catalyst oxidation. But 73% of the triphenylphosphine was ultimately oxidised, as indicated by $^{31}P$ NEAR.

During the whole run the selectivity remained around 82% (a small decrease was observed from 83% at the beginning of the run to 81% at the end). The degree of conversion was however only 63%. The results of $^{31}P$ NPR suggested that the lower catalyst activity was attributable to interaction of the tri-phenylphosphine with the rhodium atom.

These examples clearly indicate that hindered phosphines like tri(ortho-tolyl)phosphine can successfully protect the expensive phosphite hydroformylation ligands from oxidative degradation without affecting the actual hydroformylation rate. Although less hindered phosphines like triphenylphosphine also protect the phosphite ligands from oxidative degradation, they also decrease the hydroformylation rate of the catalyst.

What is claimed is:

1. A process for the preparation of an aldehyde through hydroformylation of an unsaturated organic compound in the presence of a catalyst system comprising rhodium or iridium and a multidentate organic phosphite ligand and a monodentate phosphine is present.

2. A process according to claim 1, wherein the monodentate phosphine has a steric parameter θ of between 160 and 220°.

3. A process according to claim 1, wherein the monodentate phosphine has a steric parameter θ of between 170 and 210°.

4. A process according to claim 1, wherein the monodentate phosphine is tri(ortho-tolyl)phosphine.

5. A process according to any one of claims 1–4, wherein the metal is rhodium.

6. A process according to any one of claims 1–4, wherein the hydroformylation reaction mixture contains 1–40 mol monodentate phosphine per mol multidentate phosphite ligand.

7. A process according to claim 6, wherein the hydroformylation reaction mixture contains 2–10 mol monodentate phosphine per mol multidentate phosphite ligand.

8. A process according to claim 7, wherein the hydroformylation reaction mixture contains 1–1.2 mol multidentate phosphite ligand per mol rhodium or iridium.

9. A process according to any one of claims 1–4, wherein the multidentate organic phosphite ligand is represented by the following general structure:

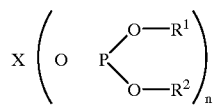
(3)

wherein n is 2–6, X is an n-valent organic bridging group and $R^1$ and $R^2$ are, independently of one another, two organic monovalent aryl groups and/or one divalent diaryl group.

10. A process according to claim 9, wherein the multidentate phosphite ligand and rhodium or iridium form a complex in the reaction zone.

11. A process according to claim 10, wherein the multidentate phosphite ligand is a bidentate phosphite ligand represented by the following general structure:

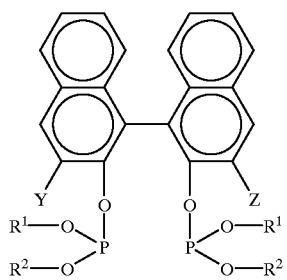

wherein Y and Z are the same or different organic groups having at least one carbon atom and $R_1$ and $R^2$ are the same or different monovalent organic aryl groups and/or one divalent diaryl group.

12. A process according to claim 11, wherein Y and Z are carboalkoxyl groups, having the formula $CO_2R$, where R is a $C_1$–$C_{20}$ alkyl or a $C_6$–C12 aryl group.

13. A process according to claim 12, wherein that $R^1$ and $R^2$ are the same or different substituted monovalent $C_6$–$C_{20}$ aryl groups containing at least one $R^4$ group at the ortho position relative to the oxygen atom, where $R^4$ is $C_1$–$C_{20}$ alkyl or $C_6$–$C_{20}$ aryl or $R^1$ and $R^2$ are monovalent $C_{10}$–$C_{20}$ aromatic fused ring systems with 2 or more rings.

14. A process according to any one of claims 1–4, wherein the unsaturated organic compound is an internally unsaturated compound having between 4 and 20 carbon atoms.

15. A process according to claim 14, wherein the organic compound is 3-pentene nitrile, 3-pentenoic acid or $C_1$–$C_6$ alkyl ester of 3-pentenoic acid.

16. A process according to claim 14, wherein the $C_1$–$C_6$ alkyl ester of 3-pentenoic acid is method-3-pentenoate or ethyl-3-pentenoate.

17. A process according to any one of claims 1–4, wherein said process is a continuous process, said catalyst system is reused in said process and fresh phosphine is continuously or batchwise added to the process.

18. A process according to any one of claims 1–4, wherein the metal is rhodium, the hydroformylation reaction mixture contains 1–1.2 mol multidentate phosphite ligand per mol rhodium, the multidentate phosphite ligand is a bidentate phosphite ligand represented by the following general structure:

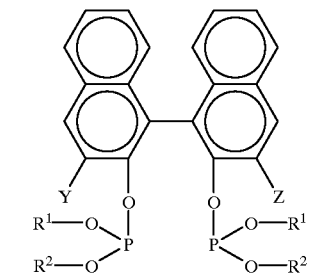

wherein Y and Z are the same or different organic groups having at least one carbon atom and $R^1$ and $R^2$ are the same or different monovalent organic aryl groups and/or one divalent diaryl group, and the unsaturated organic compound is a $C_1$–$C_6$ alkyl ester of 3-pentenoic acid.

* * * * *